US011254061B2

(12) United States Patent
Riebman et al.

(10) Patent No.: US 11,254,061 B2
(45) Date of Patent: Feb. 22, 2022

(54) SCAFFOLDS FOR IMPLANTING ABSORBABLE HEMOSTATS IN FIELD CONDITIONS

(71) Applicant: Ethicon, Inc., Somerville, NJ (US)

(72) Inventors: Jerome B. Riebman, Basking Ridge, NJ (US); Leo B. Kriksunov, Ithaca, NY (US)

(73) Assignee: Ethicon, Inc., Somerville, NJ (US)

( * ) Notice: Subject to any disclaimer, the term of this patent is extended or adjusted under 35 U.S.C. 154(b) by 477 days.

(21) Appl. No.: 15/399,968

(22) Filed: Jan. 6, 2017

(65) Prior Publication Data
US 2018/0193010 A1   Jul. 12, 2018

(51) Int. Cl.
*A61B 17/00* (2006.01)
*B29C 65/02* (2006.01)
(Continued)

(52) U.S. Cl.
CPC .......... *B29C 65/02* (2013.01); *A61B 17/0057* (2013.01); *A61F 13/00008* (2013.01);
(Continued)

(58) Field of Classification Search
CPC ...... A61B 17/0057; A61B 2017/00623; A61B 2017/00659; A61B 2017/00884;
(Continued)

(56) References Cited

U.S. PATENT DOCUMENTS 3,902,497 A * 9/1975 Casey ................. A61L 15/425
521/87
5,419,765 A   5/1995 Weldon et al.
(Continued)

FOREIGN PATENT DOCUMENTS

| WO | WO 2009/130485 | 10/2009 |
| WO | WO 2013/082073 | 6/2013 |
| WO | WO 2014/145255 | 9/2014 |

OTHER PUBLICATIONS

International Search Report re: PCT/IB2017/058215 dated Apr. 11, 2018.
Written Opinion re: PCT/IB2017/058215 dated Apr. 11, 2018.

*Primary Examiner* — Darwin P Erezo
*Assistant Examiner* — Christian D Knauss
(74) *Attorney, Agent, or Firm* — David R. Crichton; Leo B. Kriksunov

(57) ABSTRACT

The present invention relates generally to agents and devices for promoting hemostasis and, more particularly, to bioresorbable hemostatic pads or patches releasably supported on non-resorbable scaffolds for ease of delivery in the field. A sealant and/or hemostat delivery device comprises a resorbable hemostatic pad having a wound facing side and an opposite back side, with a hemostatic and/or wound sealing agent disposed on the wound facing side; a non-resorbable scaffold having an attachment zone on said scaffold; wherein said hemostatic pad is releasably attached with the back side to the attachment zone. The bond between the scaffold and the resorbable hemostatic pad or wound dressing is either (i) severed prior to removal of the scaffold or (ii) is weakened due to the adhesive bonding them together being moisture-deactivated, or (iii) is released by mechanical disentanglement.

9 Claims, 7 Drawing Sheets

(51) Int. Cl.
*B29C 65/48* (2006.01)
*A61L 15/32* (2006.01)
*A61L 24/00* (2006.01)
*A61L 15/42* (2006.01)
*A61L 24/10* (2006.01)
*A61L 24/08* (2006.01)
*A61L 15/64* (2006.01)
*A61L 15/28* (2006.01)
*A61F 13/00* (2006.01)
*A61B 17/072* (2006.01)

(52) U.S. Cl.
CPC .............. *A61L 15/28* (2013.01); *A61L 15/32* (2013.01); *A61L 15/42* (2013.01); *A61L 15/425* (2013.01); *A61L 15/64* (2013.01); *A61L 24/001* (2013.01); *A61L 24/0036* (2013.01); *A61L 24/0042* (2013.01); *A61L 24/08* (2013.01); *A61L 24/104* (2013.01); *A61L 24/106* (2013.01); *A61L 24/108* (2013.01); *B29C 65/48* (2013.01); *A61B 17/07292* (2013.01); *A61B 2017/00004* (2013.01); *A61B 2017/00526* (2013.01); *A61B 2017/00659* (2013.01); *A61B 2017/00884* (2013.01); *A61B 2017/00893* (2013.01); *A61F 2013/00463* (2013.01); *A61L 2400/04* (2013.01)

(58) Field of Classification Search
CPC .......... A61F 13/00021; A61F 13/00085; A61F 13/0259; A61F 15/005; A61F 2002/0072; A61F 13/000885; A61L 2400/04
See application file for complete search history.

(56) References Cited

U.S. PATENT DOCUMENTS

| | | | |
|---|---|---|---|
| 6,117,444 A | 9/2000 | Orgill et al. | |
| 7,604,819 B2 | 10/2009 | Huey et al. | |
| 7,666,803 B2 | 2/2010 | Shetty et al. | |
| 7,749,204 B2 | 7/2010 | Dhanaraj et al. | |
| 8,273,369 B2 | 9/2012 | Moloye-Olabisi et al. | |
| 8,329,211 B2 | 12/2012 | Moloye-Olabisi et al. | |
| 8,361,100 B2 | 1/2013 | Gabel et al. | |
| 8,372,092 B2 | 2/2013 | Gabel et al. | |
| 8,383,147 B2 | 2/2013 | Shetty et al. | |
| 8,609,129 B2 | 12/2013 | Mentkow et al. | |
| 8,637,726 B2 | 1/2014 | Spinelli et al. | |
| 9,351,883 B2 | 5/2016 | Pesnell et al. | |
| 9,358,318 B2 | 6/2016 | Gorman et al. | |
| 9,439,997 B2 | 9/2016 | Gorman et al. | |
| 2003/0073979 A1* | 4/2003 | Naimark | A61B 17/00234 604/891.1 |
| 2005/0165445 A1* | 7/2005 | Buckman | A61F 13/00 606/213 |
| 2007/0160638 A1* | 7/2007 | Mentkow | A61F 13/00034 424/422 |
| 2011/0237994 A1* | 9/2011 | Russ | A61F 13/00034 602/46 |
| 2013/0149343 A1 | 6/2013 | Pesnell et al. | |
| 2013/0253462 A1* | 9/2013 | Robson | A61B 42/10 604/385.03 |
| 2013/0261660 A1* | 10/2013 | McKay | A61F 2/4611 606/213 |
| 2013/0289468 A1* | 10/2013 | Young | A61F 13/00068 604/11 |
| 2014/0243726 A1* | 8/2014 | San Antonio | A61L 15/325 602/50 |
| 2015/0017225 A1* | 1/2015 | Hubbell | A61L 15/64 424/444 |
| 2015/0238366 A1* | 8/2015 | Pesnell | A61L 15/32 427/2.31 |
| 2015/0367019 A1* | 12/2015 | MacPhee | A61L 15/32 424/445 |
| 2016/0022861 A1* | 1/2016 | Macphee | A61L 24/0042 604/15 |

* cited by examiner

FIG. 1
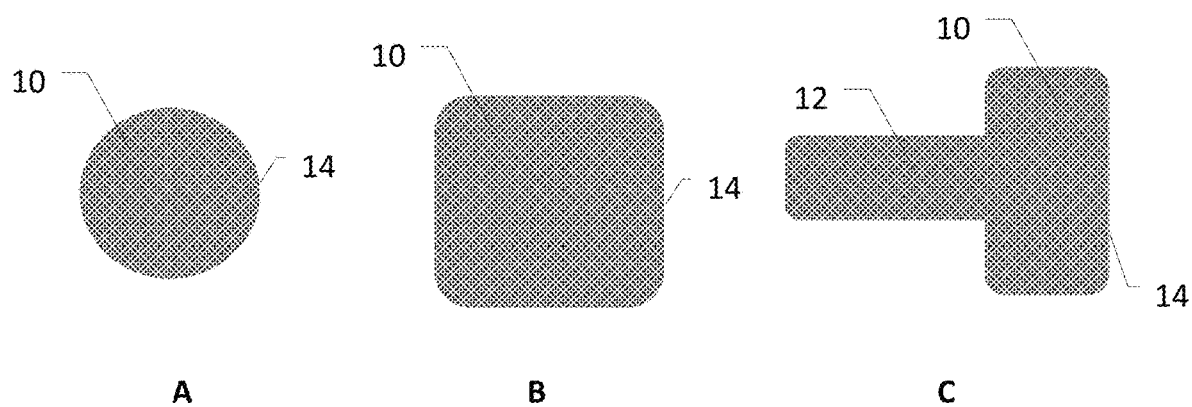
A    B    C
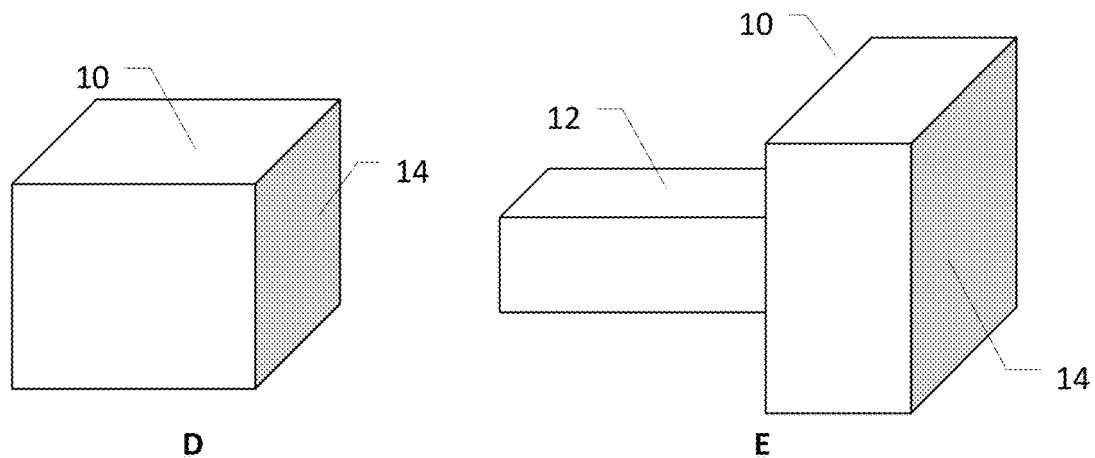
D    E

FIG. 2
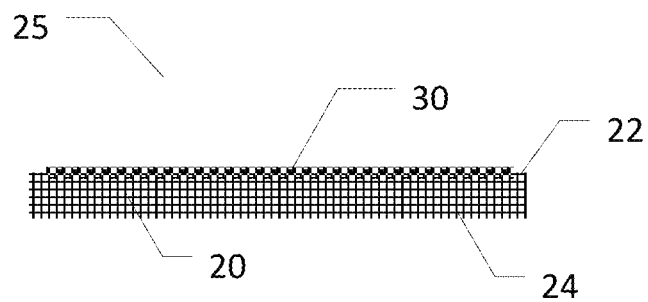
FIG. 3
A
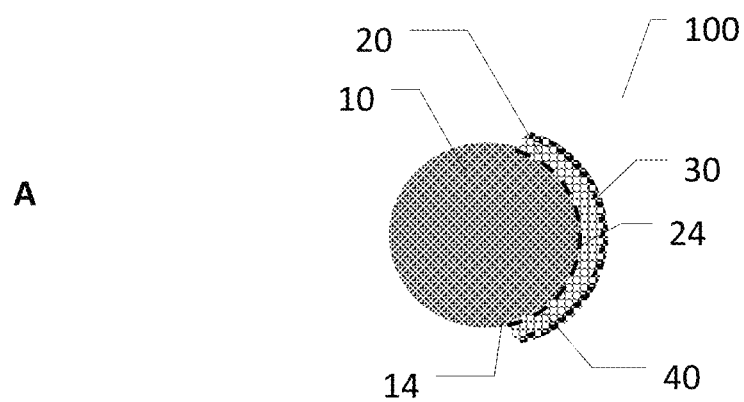
B
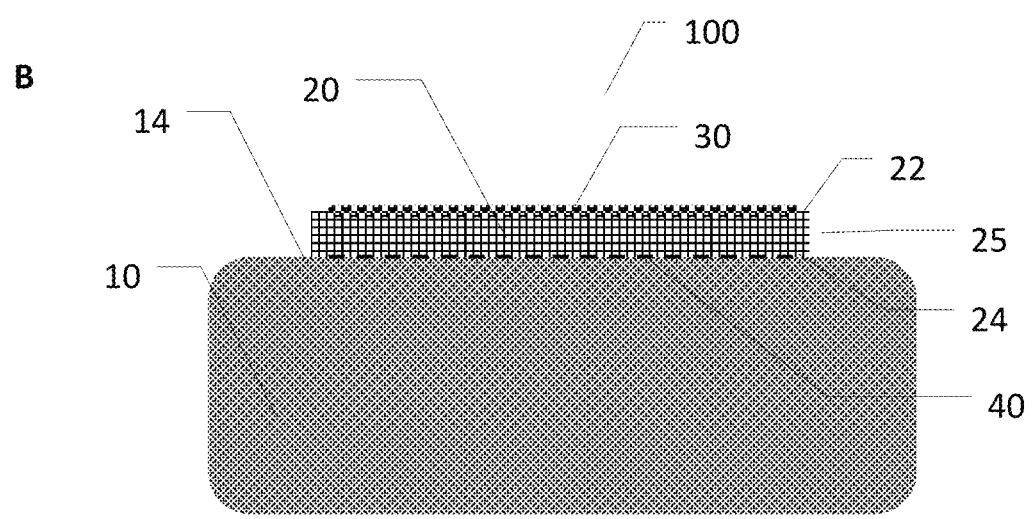

SCAFFOLDS FOR IMPLANTING ABSORBABLE HEMOSTATS IN FIELD CONDITIONS

FIELD OF THE INVENTION

The present invention relates generally to agents and devices for promoting hemostasis and, more particularly, to bioresorbable hemostatic pads or patches releasably supported on non-resorbable scaffolds for ease of delivery.

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

Prolonged or uncontrolled bleeding following trauma or after surgery of the cardiovascular system, liver, kidney, spleen, and other organs is a serious complication associated with significant morbidity, mortality, and cost of care. Meticulous surgical technique is essential for primary hemostasis, but when conventional techniques such as compression, ligation, clipping, and electrocautery are impractical or ineffective, topical hemostatic agents are indispensable and relied upon to help control blood loss.

The control of bleeding is essential and critical in surgical procedures to minimize blood loss, to reduce post-surgical complications, and to shorten the duration of the surgery in the operating room. In an effort to address the above-described problems, materials have been developed for controlling excessive bleeding. Many approved and investigational topical hemostats have been described in the literature, including oxidized regenerated cellulose (ORC), collagen, gelatin, fibrinogen, thrombin, as well as other biological, natural, synthetic, or inorganic compounds. Some of these can at least partially rely on physical means for passive coagulation while others provide biologically active components of the clotting cascade. The latest generation of topical hemostats combines both active and passive mechanisms of action.

Topical bioabsorbable hemostats (TAHs) are widely used in surgical applications. TAHs encompass products based on various woven or non-woven fabrics or sponges, typically made of at least partially resorbable materials, ranging from natural to synthetic polymers and combinations thereof, including lactide-glycolide based co-polymers such as Polyglactin 910, oxidized cellulose (OC), oxidized regenerated cellulose (ORC), gelatin, collagen, chitin, chitosan, etc. Hemostatic formulations applied in the form of dry powder, semi-liquid paste, liquid formulation, or optionally disposed on a supporting scaffold such as bioabsorbable fabric scaffold. To improve the hemostatic performance, scaffolds based on the above materials can be combined with various sealing or clotting factors, such as biologically-derived clotting factors, such as thrombin and/or fibrinogen.

Some currently utilized hemostatic wound dressings include knitted or non-woven fabrics comprising carboxylic-oxidized cellulose. Examples of such hemostatic wound dressings are commercially available include SURGICEL® Original absorbable hemostat; SURGICEL NU-KNIT® absorbable hemostat; and SURGICEL® FIBRILLAR™ absorbable hemostat; all available from Ethicon, Inc., Somerville, N.J., a Johnson & Johnson Company. Other currently utilized hemostatic wound dressings comprise gelatin or collagen, for example Surgiflo® Hemostatic Matrix absorbable hemostat available from Ethicon, Inc.

Some currently utilized hemostatic wound dressings and sealants comprise blood clotting factors such as thrombin and/or fibrinogen, which can be animal derived or human origin blood clotting factors. Such biologic factors-containing hemostatic wound dressings and sealants can be in the form of liquid sprays, such as sealant EVICEL® Fibrin Sealant (Human), available from Ethicon, Inc., Somerville, N.J.

Some currently utilized hemostatic wound dressings and sealants comprise blood clotting factors such as thrombin and/or fibrinogen which are dispersed in a semi-solid carrier, such as gelatin, or in or on a solid substrate, such as the EVARREST® Fibrin Sealant Patch.

Decreasing the time to achieve hemostasis has great clinical significance to save blood loss and speed up the procedure. Some of current products on the market in case of mild to moderate bleeding achieve hemostasis in a time frame from about 4 to 10 minutes. In addition, some products do not have ideal handling characteristics as they wrinkle and fold during surgical procedures especially in the presence of blood or other fluids. A medical need remains for hemostatic devices that have better mechanical properties, particularly for use in laparoscopic procedures and/or in the field far from a fully equipped surgical suite. There is a clear medical need to achieve faster hemostasis to reduce blood loss during surgery as well as a desire to provide improved handling performance and an improved ability for TAH to stay in place after application.

U.S. Patent Publication No. 2007/0160638 entitled "Hemostatic agent delivery system" discloses a hemostatic agent delivery system comprising: at least one hemostatic agent structured to facilitate blood clotting, a delivery assembly structured to permit disposition of an amount of said hemostatic agent directly proximate a hemorrhage site, said delivery assembly structured to releasably contain said amount of said hemostatic agent, said delivery assembly comprising a release member disposed in an overlying relation to a support member and attached about a periphery thereof, said release member and said support member cooperatively structured to at least temporarily contain said amount of said hemostatic agent therebetween, and said release member comprising a soluble material structured to dissolve and release said amount of said hemostatic agent upon disposition directly proximate to the hemorrhage site.

U.S. Pat. No. 8,361,100 entitled "Applicator instruments for the delivery, deployment, and tamponade of hemostats and methods therefor" discloses an instrument for controlling bleeding comprising: an intermediate shaft having a proximal end, a distal end, a longitudinal axis extending between the proximal and distal ends of said intermediate shaft, and a central lumen extending to the distal end; an inner shaft telescopically received within the central lumen of said intermediate shaft, said inner shaft having a proximal end and a distal end that extends distally from said outer shaft; an outer shaft having a proximal end, a distal end, and a central lumen extending to the distal end thereof, wherein said intermediate and inner shafts are disposed within the central lumen of said outer shaft; a balloon having a proximal end secured to the distal end of said intermediate shaft and a distal end secured to said inner shaft, wherein the distal end of said balloon is inverted and the inverted distal end is secured to the distal end of said inner shaft; a hemostat distal to and in contact with the distal end of said balloon; a first actuator for inflating said balloon; a second actuator for moving the distal ends of said intermediate and inner shafts relative to one another for changing the shape of said balloon, wherein upon inflation said inflated balloon has a leading face that forms a distal-most end of said instrument and said inflated balloon has a major axis that is perpendicular to the longitudinal axis of said intermediate shaft; and a third actuator coupled with said outer shaft for moving the distal end of said outer shaft proximally relative to the distal ends of said intermediate and inner shafts.

U.S. Pat. No. 5,419,765 entitled "Wound treating device and method for treating wounds" discloses a wound treating device adapted to be positioned adjacent to an aperture in a blood vessel comprising: an elongated tube having proximal and distal end portions, said tube comprising at least first and second lumens extending between said proximal and distal ends; said first lumen adapted to receive a flow control device partially positioned within the blood vessel for providing local flow control at the aperture in the blood vessel; a flexible membrane carried generally adjacent said distal end portion and movable between a retracted position and an inflated position to form a balloon-like projection at said distal end; and a wound treating agent releasably predisposed within said elongated tube and releasable into the vicinity of the aperture in the blood vessel.

U.S. Pat. No. 8,372,092 entitled "Applicator Instruments Having Protective Carriers for Hemostats and Methods Therefore" discloses an instrument for delivering a hemostat comprising: an outer shaft having a proximal end and a distal end; a balloon disposed at the distal end of said outer shaft; a hemostat disposed distal to the distal end of said outer shaft and distal to said balloon; and a fluid-resistant element connected to and extending distally from the distal end of said outer shaft and surrounding said balloon and said hemostat, said fluid-resistant element having a breakable, fluid-resistant seal at a distal end thereof, wherein said outer shaft and said fluid resistant element connected to the distal end of said outer shaft slide together, axially toward a proximal end of said instrument and relative to said hemostat for delivering said balloon and said hemostat through said fluid resistant seal.

U.S. Pat. No. 6,117,444 entitled "Polyethylene glycol/microfibrillar collagen composite serves as a resorbable hemostatic agent" discloses a resorbable hemostatic bone agent comprising about 65% to about 95% by weight delivery component and about 5% to about 25% by weight hemostatic component, wherein said hemostatic component consists essentially of a microfibrillar collagen and wherein said delivery component is in a semi-solid state at temperatures ranging from 0° C. to 45° C.

U.S. Patent Publication No. 2013/0149343 entitled "Hemostatic Bioabsorbable Device with Polyethylene Glycol Binder" discloses hemostatic pad comprising: a) a bioabsorbable scaffolding material; b) a thrombin powder, c) a fibrinogen powder, and d) a meltable binder powder that is a hydrophilic, biocompatible, and bioabsorbable material having a melting point from about 25° C. to about 100° C., wherein said thrombin and fibrinogen powders are disposed on the bioabsorbable scaffolding material and the meltable binder powder bonds the thrombin powder and the fibrinogen powder to the bioabsorbable scaffolding material but does not fully envelop the lyophilized thrombin powder and/or the lyophilized fibrinogen.

U.S. Patent Publication No. 2015/0017225 entitled "Hemostatic Pad Assembly Kit and Method" discloses a hemostatic wound treatment device comprising: a bioabsorbable scaffold having a wound facing surface and an opposing surface; said scaffold wetted with a biocompatible liquid that is not blood or plasma; and a hemostatic powder that adheres by moisture to at least the wound facing surface of said bioabsorbable scaffold.

U.S. Pat. No. 8,609,129 entitled "Hemostatic agent composition, delivery system and method" discloses a system for delivering a hemostatic agent to a wound, the system comprising: a composition of a hemostatic hectorite clay material combined with a glycol humectant in a stable suspension, said glycol humectant in said stable suspension acting to create a hydrophilic matrix and said composition including: a) 40-70% propylene glycol; b) 20-40% hectorite clay; c) 5-15% $H_2O$; d) 1-10% Carbomer; and e) 1-10% triethanolamine; and an absorbent mesh fabric having said composition embedded therein to adhere to the wound, permit at least some of said composition to come into contact with a bleeding source, effect hemostasis of bleeding, accelerate stable clotting, prevent displacement of said composition by arterial pressure and be easily removed; said stable suspension allowing for increased embedment in said mesh fabric matrix and acting to create elasticity providing wound conformation.

U.S. Pat. No. 8,637,726 entitled "Shape and pressure adjustable dressing" discloses a dressing for covering a wound, the dressing comprising: a first component having a first shape with a first dimension; a second component releasably attached to a first surface of the first component to maintain the first component in a second shape different from the first shape, the second shape having a second dimension longer than the first dimension; and an adhesive disposed on a surface of the first component different from the first surface for attaching the first component to the wound such that the second component can be released from the first component to allow the first component to take the first shape to apply a pressure to portions of the skin surrounding the wound to close the wound.

U.S. Pat. No. 7,604,819 entitled "Clay-based hemostatic agents and devices for the delivery thereof" discloses a device capable of providing a hemostatic effect on bleeding, said device comprising: a gauze substrate; a clay material disposed on said gauze substrate; and a water-soluble polyol binder disposed on said gauze substrate to bind said clay material to said gauze substrate; wherein the gauze substrate initially exists separately from the clay material before the gauze and the clay material are combined; wherein the polyol binder has an effect of substantially suppressing clay dust; and wherein said device is not saturated with a liquid and the device is configured such that when treating bleeding, application of said device is capable of causing at least a portion of said clay material to come into contact with blood to assist in accelerating clotting.

In adverse conditions in the field (i.e. outside of a surgical suite, such as at the accident site/first responder use, in the military theater, at night, etc.) there is a need in improved hemostatic dressings. In applications of hemostatic pads or patches to deep wounds in the field, the practitioners face challenges related to positioning the pad onto or into the deep wound, applying tamponade, and positioning the pad with the active side towards the wound. There is a need to provide improved hemostatic patches and pads for use in the field.

SUMMARY OF THE INVENTION

Briefly, the present invention in one aspect relates to sealant and/or hemostat delivery device, comprising: a resorbable hemostatic pad having a wound facing side and an opposite back side, with a hemostatic and/or wound sealing agent disposed on the wound facing side; a non-resorbable scaffold having an attachment zone on the scaffold; wherein the hemostatic pad is releasably attached with the back side to the attachment zone. In some aspects, the scaffold is absorbent and surgically compatible material. In some aspects, the scaffold comprises a handle configured for deep wound applications. In some aspects, the scaffold comprises a reinforcing member or spreading member. In some aspects, the scaffold comprises a material expanding upon exposure to water or bodily fluids.

In one embodiment, the hemostatic pad is attached to the scaffold with a water soluble adhesive material disposed at least partially between the hemostatic pad and the scaffold, wherein the hemostatic pad is configured to be releasable from the scaffold upon contact with body fluids. In some aspects, the water soluble adhesive material comprises polyethylene glycol. In some aspects, the water soluble adhesive material has a melting point between about 50° C. and about 75° C.

In some aspects, there is provided a method of making the sealant and/or hemostat delivery device, comprising: positioning the water soluble adhesive material between the back side and the attachment zone; heating the scaffold and the hemostatic pad with the water soluble adhesive material sandwiched therebetween; melting the water soluble adhesive material; cooling the scaffold and the hemostatic pad with the water soluble adhesive material sandwiched therebetween; allowing he water soluble adhesive material to solidify; thus bonding the resorbable hemostatic pad to the scaffold.

In some aspects, there is provided a method of using the sealant and/or hemostat delivery device, comprising: applying the delivery device to a wound by contacting wound facing side with the wound; keeping the delivery device in contact with the wound for a time sufficient to adhere the resorbable hemostatic pad to the wound; keeping the delivery device in contact with the wound until the adhesive loses at least 50% of strength; releasing the resorbable hemostatic pad from the scaffold; removing the scaffold and leaving the resorbable hemostatic pad on the wound.

In one embodiment, the hemostatic pad is attached to the scaffold with a string that is releasably stitched though the hemostatic pad and through the scaffold and optionally anchored in the scaffold; with a portion of the string is exposed on a side opposite the attachment zone.

In one embodiment, the scaffold further comprises at least two slits formed in the attachment zone; wherein the hemostatic pad comprises at least two flaps on a periphery thereof, with the flaps inserted onto the slits; wherein the slits releasably engage the flaps releasably immobilizing the hemostatic pad on the scaffold.

BRIEF DESCRIPTION OF THE FIGURES

FIGS. 1 (A-E) show delivery and application scaffolds in schematic cross-sectional views and schematic perspective views.

FIG. 2 shows resorbable hemostatic dressing, patch or pad in a schematic cross-sectional view.

DETAILED DESCRIPTION OF THE INVENTION

Figure 3:
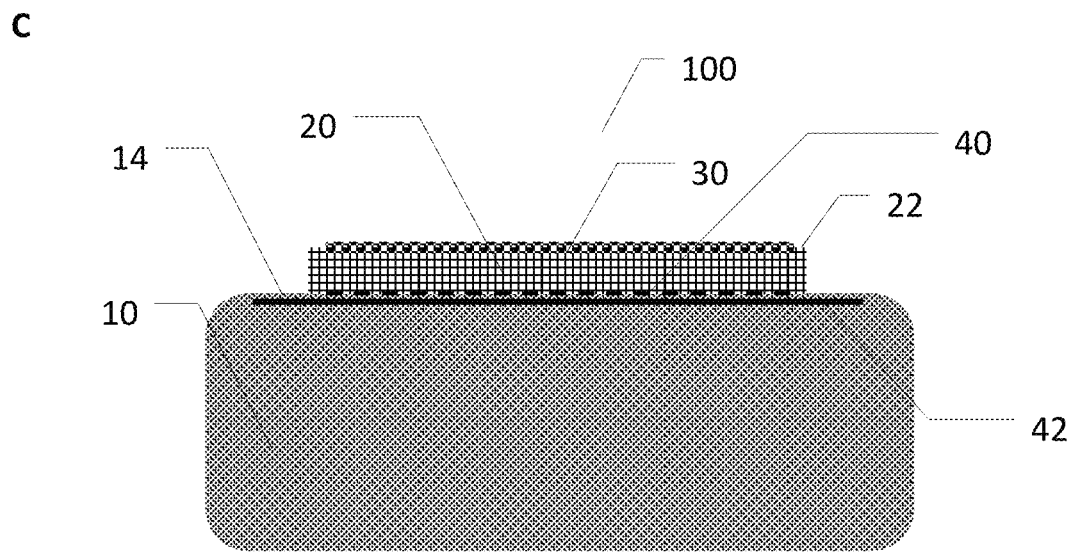
FIGS. 3 (A-C) show schematic cross-sectional views of embodiments of sealant and/or hemostat delivery devices.

Briefly, the present invention relates to bioresorbable hemostatic and/or wound sealing pads or patches releasably supported on non-resorbable delivery and application scaffolds. In one aspect, an optionally absorbent and non-resorbable applicator or scaffold is used to releasably support a hemostatic absorbable wound dressing while applying it to the deep wound and performing the initial tamponade and/or temporary wound packing, with the scaffold removed after the hemostasis is achieved leaving the absorbable wound dressing on the wound. The bond between the scaffold and the absorbable wound dressing is either (i) severed prior to removal of the scaffold or (ii) is weakened due to the adhesive bonding them together being moisture-deactivated, or (iii) is released by mechanical disentanglement.

Referring now to FIG. 1, scaffolds 10 are presented in schematic cross-sectional views (FIG. 1A, 1B, 1C) and in a schematic perspective view (FIG. 1D, 1E). Scaffold 10 comprises a body of any biocompatible material, such as a bundle or a stack of cloth or fabric, e.g. medical gauze, and can be made of any polymer, synthetic, natural, or combinations thereof, such as cotton, linen, viscose, gelatin, collagen, polyester, polyethylene, polypropylene, silicone, etc. Scaffold 10 can be of any shape which is easy to handle and apply to a wound, particularly to a surface wound or a deep wound, including cylindrical, spherical (as shown in FIG. 1A), elliptical, cuboid or rectangular/brick-shaped (as shown in FIGS. 1B, 1D), cubic, cuboid with a handle 12 (as shown in FIG. 1C, 1E), etc. Cuboid scaffolds of FIGS. 1B, 1D can have Width-Length-Thickness dimensions (mm) of from about 20-20-3 to about 200-200-50. In some embodiments, the dimensions are 20-50-4; 40-40-3; 50-100-5; 100-100-10; 150-100-25 and similar. Attachment zone 14 is a portion of the surface of scaffold 10 surface where a hemostatic pad is releasably attached to scaffold 10.

Handle 12 is configured for ease of use in deep wound applications and has aspect ratio (length to cross-sectional dimension or length to diameter) of from 2 to about 15. In one embodiment handle is cylindrical with diameter 8 mm-30 mm having the length of 60 mm-150 mm. In one embodiment handle is 100 mm long and 15 mm in diameter.

Scaffolds 10 are used as a temporary support and are not left in the wound or on the wound for extended period of time, i.e. in excess of several hours. More typically, scaffolds 10 are to be removed within 1 hour of application, such as within 1, 2, 3, 5, 10, 20, 30, 45, 60 minutes after application, such as within 5 minutes. Scaffolds 10 can be bioresorbable or non-bioresorbable. In a preferred embodiment, scaffolds 10 are non-bioresorbable. In a preferred embodiment, scaffolds 10 are absorbent materials capable of absorbing large quantity of fluids as percentage of the weight of scaffold 10, such from 50% to 1000% or more by weight of scaffold 10. Scaffolds 10 are not balloons in that they are not inflatable or deflatable. In some embodiments, scaffold 10 comprises a material that expands upon exposure to water or bodily fluids. In some embodiments, scaffold comprises non-absorbable foam.

Referring now to FIG. 2, a resorbable hemostatic dressing, patch or pad 25 is shown in a schematic cross-sectional view, pad 25 comprising a thin, flat, flexible, conformable resorbable support 20 having a wound facing side 22 and an opposite back side 24, with a hemostatic and/or wound sealing agent 30 disposed on wound facing side 22. Resorbable hemostatic pads 25 can be of any shape, such as square, rectangular, circular, oval, etc. Rectangular hemostatic pads 25 can have side dimensions from about 20 mm to about 200 mm and having thickness from about 0.5 mm to about 10 mm, such as 1 mm, 2 mm, 3 mm, 4 mm. The area of hemostatic pads 25 can be from about 4 cm$^2$ to about 400 cm$^2$ or more.

Resorbable hemostatic pads 25 are known in the art, with hemostatic and/or wound sealing agent 30 being a synthetic material or a biologic material such as fibrinogen and/or thrombin. Resorbable support 20 is exemplified by a woven or non-woven fabric, cloth, or film, which can be made of oxidized cellulose, oxidized regenerated cellulose, collagen, gelatin, chitosan, synthetic absorbable polyesters, such as poly-dioxanone, poly-caprolactone, lactide, glycolide, PLGA, Polyglactin 910, and any other known in the art natural or synthetic resorbable polymers and their combinations, including multi-layer assemblies and combinations, and can be porous or non-porous.

According to one embodiment of the present invention, resorbable support 20 is exemplified by multi-layer or single layer reinforced fabric as described in U.S. Pat. No. 7,666,803 "Reinforced absorbable multilayered fabric for use in medical devices", U.S. Pat. No. 7,749,204 "Reinforced absorbable multilayered fabric for use in tissue repair and regeneration", U.S. Pat. No. 8,273,369 "Reinforced absorbable synthetic matrix for hemostatic applications", U.S. Pat. No. 8,329,211 "Reinforced absorbable multi-layered fabric for hemostatic applications", U.S. Pat. No. 8,383,147 "Reinforced absorbable synthetic matrix for hemostatic applications", which are incorporated by reference herein for all purposes in their entirety.

Agent 30 can be in a dry or semi-dry form, and preferably activated upon contact with physiological fluids, such as blood. Upon exposure to such fluids, agent 30 becomes adhesive as to the moist tissue surface to which it is applied, such as to the surface of a bleeding wound, preferably providing sealing and/or hemostatic action. In some embodiments, agent 30 comprises fibrinogen, thrombin, chitosan, gelatin, oxidized cellulose, oxidized regenerated cellulose, any synthetic moisture-activated adhesive, and combinations thereof. According to one embodiment of the present invention, resorbable hemostatic pads 25 are exemplified by a fibrin pad as described in U.S. Pat. No. 9,439,997 "Reinforced Absorbable Multilayered Hemostatic Wound Dressing", U.S. Pat. No. 9,358,318 "Method of making a reinforced absorbable multilayered hemostatic wound dressing", incorporated by reference herein for all purposes in their entirety.

Referring now to FIG. 3, a schematic cross-sectional view is shown of embodiments of the present invention with sealant and/or hemostat delivery devices 100 comprising resorbable hemostatic pads 25 which are releasably attached to scaffolds 10. FIG. 3A shows cylindrical, spherical, or elliptical scaffold 10, and FIG. 3B shows cuboid scaffold 10.

Back side 24 of resorbable support 20 is releasably attached to attachment zone 14 of on the surface of scaffold 10, with agent 30 exposed on the surface of hemostat delivery device 100. Resorbable support 20 covers all or a major portion of attachment zone 14 or of the wound facing side of scaffold 10.

The releasable attachment means or mechanism 40 is shown by a dotted line in FIG. 3 and is configured to release resorbable hemostatic pad 25 from scaffold 10 once positioned on a wound and adequately adhering to the wound. The release of resorbable hemostatic pad 25 from scaffold 10 is effected by (i) severing a mechanical connection mechanism 40 or (ii) weakening due to the adhesive mechanism 40 being moisture-deactivated, or dissolves in water and/or wound exudates, or (iii) via release by mechanical disentanglement of mechanism 40.

Non-absorbable scaffold 10 can be porous or non-porous. Scaffold 10 can be used to apply tamponade to a wound. For porous scaffold 10, scaffold 10 can absorb excess exudates from a wound, such as blood. In a preferred embodiment, scaffold 10 is absorbs exudates from a wound. In an alternative embodiment, scaffold 10 is non-porous and non-permeable to wound exudates. Referring now to FIG. 3C, an embodiment of FIG. 3B is shown, with a porous scaffold 10, but having a barrier layer 42 covering attachment zone 14. Barrier layer 42 prevents any wound exudates, such as blood, from penetrating into porous scaffold 10. Barrier layer 42 is a coating or a layer of liquid-impervious material such as polyethylene, polypropylene, gelatin, etc.

Figure 4:
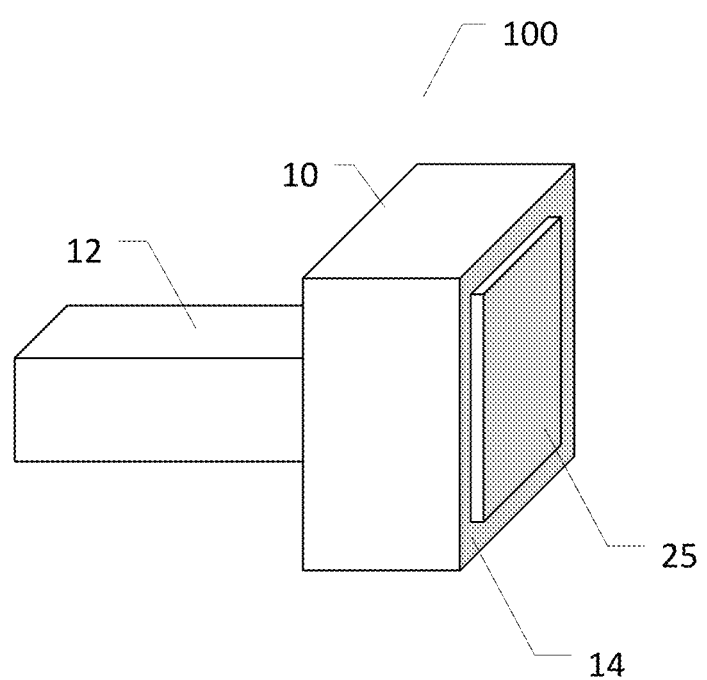
FIG. 4 shows a schematic perspective view of an embodiment of sealant and/or hemostat delivery device.

Referring now to FIG. 4, a schematic perspective view of embodiment of hemostat delivery device 100 is shown, with scaffold 10 having handle 12 and resorbable hemostatic pad 25 releasably attached onto attachment zone 14. Resorbable hemostatic pad 25 can cover all or a major portion (as shown in FIG. 4) of the wound facing side or attachment zone 14 of scaffold 10. In one embodiment (not shown) resorbable hemostatic pad 25 extends around and beyond wound facing side or attachment zone 14 of scaffold 10.

Figure 5:
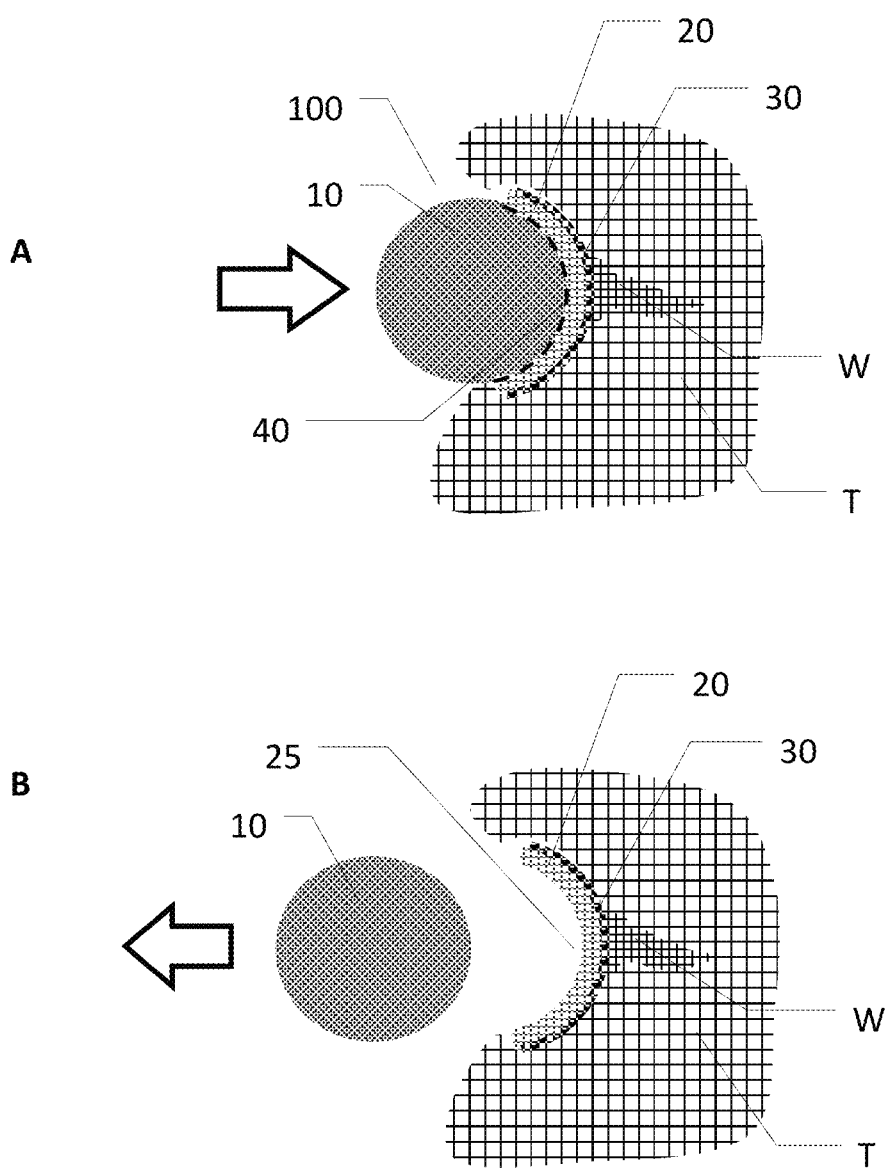
FIGS. 5 (A-B) show schematic cross-sectional views of sealant and/or hemostat delivery devices in operation.

Referring now to FIG. 5, a schematic cross-sectional view of hemostat delivery devices 100 in operation is shown. Turning to FIG. 5A, in operation, hemostat delivery device 100 is applied to a wound W in tissue T in the direction of arrow, with the healthcare practitioner handling hemostat delivery device 100 by holding it by scaffold 10 area not covered by resorbable hemostatic pad 25. Hemostat delivery device 100 is applied to wound W with agent 30 towards wound W, with tamponade or pressure applied in the direction shown by arrow. Scaffold 10 is used to position resorbable hemostatic pad 25 on the wound with agent 30 touching the wound and to apply tamponade. Agent 30 reacts with blood or any other wound exudates to adhere resorbable hemostatic pad 25 to the wound W.

Simultaneously, the releasable attachment mechanism 40 releases resorbable hemostatic pad 25 from the scaffold, automatically or due to the action of health practitioner. As shown in FIG. 5B, after resorbable hemostatic pad 25 has reliably adhered to the wound, scaffold 10 is then pulled from wound W in the direction of arrow, separating scaffold 10 from resorbable hemostatic pad 25 and leaving resorbable hemostatic pad 25 on wound W providing sealing and/or hemostasis. Scaffold 10 is then discarded.

Figure 6:
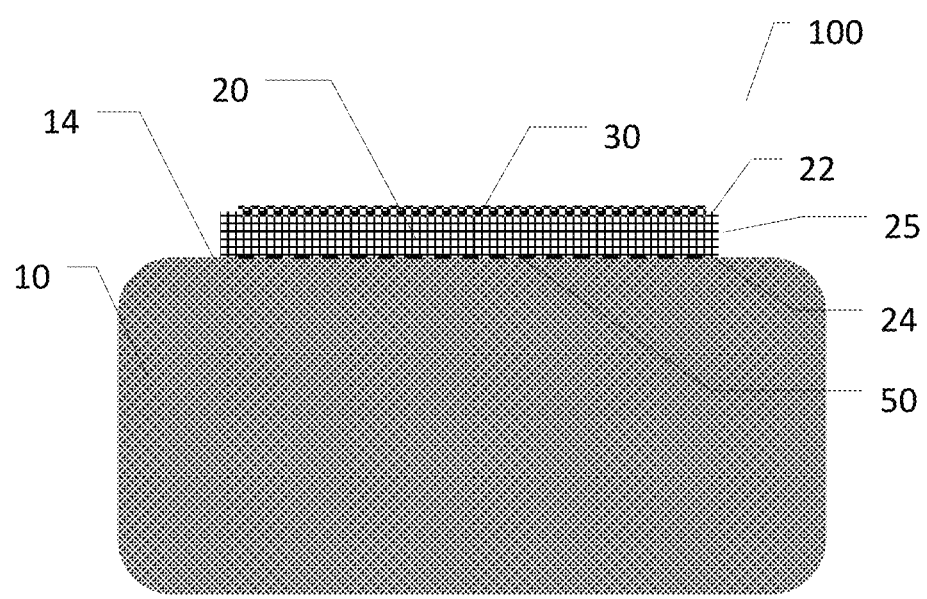
FIG. 6 shows a schematic cross-sectional view of an embodiment of sealant and/or hemostat delivery device.

Referring now to FIG. 6, a schematic cross-sectional view is shown of a preferred embodiment of the present invention showing hemostat delivery device 100 comprising resorbable hemostatic pad 25 releasably attached to scaffold 10. Back side 24 of resorbable support 20 is releasably attached to attachment zone 14 of on the surface of scaffold 10, with agent 30 exposed on the surface of hemostat delivery device 100. The releasable attachment mechanism 50 is shown by a dotted line 50 and comprises water-soluble adhesive 50. Adhesive 50 is configured to release resorbable hemostatic pad 25 from scaffold 10 once positioned on a wound with bond between resorbable hemostatic pad 25 and scaffold 10 weakening due to the adhesive 50 dissolving in water or wound exudates and/or being moisture-deactivated. As blood and/or exudates from wound W penetrate into resorbable support 20, moisture penetrates to the interface between the surface of scaffold 10 and back side 24 of resorbable support 20 where adhesive 50 is disposed, dissolving adhesive 50 thus releasing resorbable hemostatic pad 25 from scaffold 10. Agent 30 reacting with blood or any other wound exudates results in resorbable hemostatic pad 25 adherence to the wound. At least partial dissolution of adhesive 50 releases resorbable hemostatic pad 25 from scaffold 10, whereby scaffold 10 can then be removed and discarded, while leaving resorbable hemostatic pad 25 on the wound.

The mechanism of bonding of resorbable hemostatic pad 25 to scaffold 10 utilizes bonding mechanism that can be established in the absence of water or moisture contacting agent 30, as presence of water or moisture will activate and potentially render inoperable agent 30. In one embodiment, the bonding is established by a rapidly water soluble, low temperature melting material, such as low MW polyethylene glycol (PEG).

According to one embodiment of the present invention, meltable PEG is applied at ambient temperature in a non-molten format, as a powder or as a film, to attachment zone 14 on the surface of scaffold 10, to back side 24 of resorbable support 20, or to both attachment zone 14 and back side 24. Resorbable hemostatic pad 25 is then positioned on scaffold 10 with back side 24 in contact with attachment zone 14, with meltable PEG sandwiched between back side 24 and attachment zone 14, and the construct is exposed to heating to temperature that exceeds melting point of PEG, but below the temperature that can damage agent 30. Heating can be performed in an oven, optionally under inert atmosphere or under vacuum. Heating can be also performed using electromagnetic heating such as microwave or radiofrequency (RF) heating, which is specifically targeting PEG as polar material and heating other components to a lesser degree if at all. Immediately after PEG begins to soften into a viscous, malleable form, heating is stopped and PEG is allowed to cool and solidify thus bonding resorbable hemostatic pad 25 to scaffold 10.

In an alternative embodiment, meltable PEG is applied in a molten form as liquid or semi-liquid material, to attachment zone 14 on the surface of scaffold 10, to back side 24 of resorbable support 20, or to both attachment zone 14 and back side 24. Back side 24 and/or attachment zone 14 are then allowed to cool resulting in solidifying of PEG applied to attachment zone 14 and/or to back side 24. Resorbable hemostatic pad 25 is then positioned on scaffold 10 with back side 24 in contact with attachment zone 14, with meltable PEG sandwiched between back side 24 and attachment zone 14, and the construct is exposed to heating to temperature that exceeds melting point of PEG, but below the temperature that can damage agent 30. Immediately after PEG softens, heating is stopped and PEG is allowed to cool and solidify thus bonding resorbable hemostatic pad 25 to scaffold 10.

In one embodiment, meltable PEG powder can be applied by using a non-aqueous solvent, low boiling solvent, such as the hydrofluoroether (HFE) fluid from 3M Novec Engineered Fluid HFE-7000, 1-methoxyheptafluoropropane that is commercially available from 3M Corporation. HFE-7000 is an inert, nonflammable, low boiling point fluid. HFE-7000 can be used to apply a suspension of PEG as an inert delivery vehicle onto scaffold 10 and/or onto back side 24 and then to be substantially completely removed by evaporation, leaving PEG powder on scaffold 10 and/or on back side 24.

Alternatively, solvents in which PEG is soluble can be utilized, such as water, alcohols, etc. In this embodiment, PEG solution such as an aqueous or ethanol-based solution is applied onto attachment zone 14 of on the surface of scaffold 10, such as by spray or by dipping. The solvent is then allowed to evaporate leaving behind the meltable PEG material, with at least a portion of meltable material exposed on the surface of scaffold 10 on attachment zone 14, with evaporation of solvent performed over time, at elevated temperature, in vacuum, via freeze drying, and/or by any other known means. After that bonding of resorbable hemostatic pad 25 to scaffold 10 is performed as described above by heating and transiently melting PEG and then cooling PEG thus bonding resorbable hemostatic pad 25 to scaffold 10.

Any meltable, water soluble, biologically compatible and bioabsorbable material can be used in practicing the present invention, provided that it is solid at ambient temperature and has a melting temperature below the temperature of appreciable thermal damage to agent 30. The preferred binder is based on polyethylene glycol (PEG) having an average molecular weight of 1000 to 20,000 Daltons, and more preferably PEG having average molecular weight of 3000 to 8000. In one embodiment, PEG 3000 can be used, obtained from Fluka, with melting point of about 56-59° C., having and a number average particle size of 45 microns as described in U.S. Pat. No. 9,351,883, "Hemostatic bioabsorbable device with polyethylene glycol binder", which is incorporated herein by reference in its entirety. In one embodiment, the binder particles have a particle size in the range of about 25-60 microns, more preferably in the range of 35-55 microns, for at least 95% of the particles by number.

Many sources of PEG are available. For instance, Sigma-Aldrich lists PEG having Average Molecular Weight: 3,350 (3,000-3,700), CAS Number: 25322-68-3, and Melting Point: 54-58° C., as soluble in water (approximately 670 mg/ml, 20° C.) and also soluble in many polar solvents such as acetone, alcohols, and chlorinated solvents but insoluble in nonpolar solvents such as hydrocarbons.

Other materials can be used as adhesive 50, both low melting and not low-melting materials, including PVA, sucrose (optionally with citric acid); sodium chloride; casein, gelatin, albumin.

In some aspects, non low temperature meltable adhesives or high temperature melting adhesives are applied in non-aqueous carriers (absolute ethanol, HFE) to avoid reactivity of agent 30 and upon evaporation of the solvent, the adhesive attaches the resorbable hemostatic pad 25 to scaffold 10. In these embodiments, both resorbable hemostatic pad 25 and scaffold 10 are wetted with non-aqueous carriers containing dissolved adhesives, resorbable hemostatic pad 25 positioned on scaffold 10, and upon evaporation of the solvent the selected adhesive secures resorbable hemostatic pad 25 back side 24 to scaffold 10.

In operation, and upon exposure to moisture or blood, the adhesive loses at least 50% of strength within several seconds or several minutes after application to the wound, weakening the bond and releasing the absorbable wound dressing from the scaffold. In a preferred embodiment, adhesive loses at least 80% or at least 90% of strength upon exposure to moisture or blood on wound W. Adhesive loss of at least 50% or 90% of strength means that the force required to separate resorbable hemostatic pad 25 from scaffold 10 is decreased by at least 50% or 90% respectively.

Figure 7:
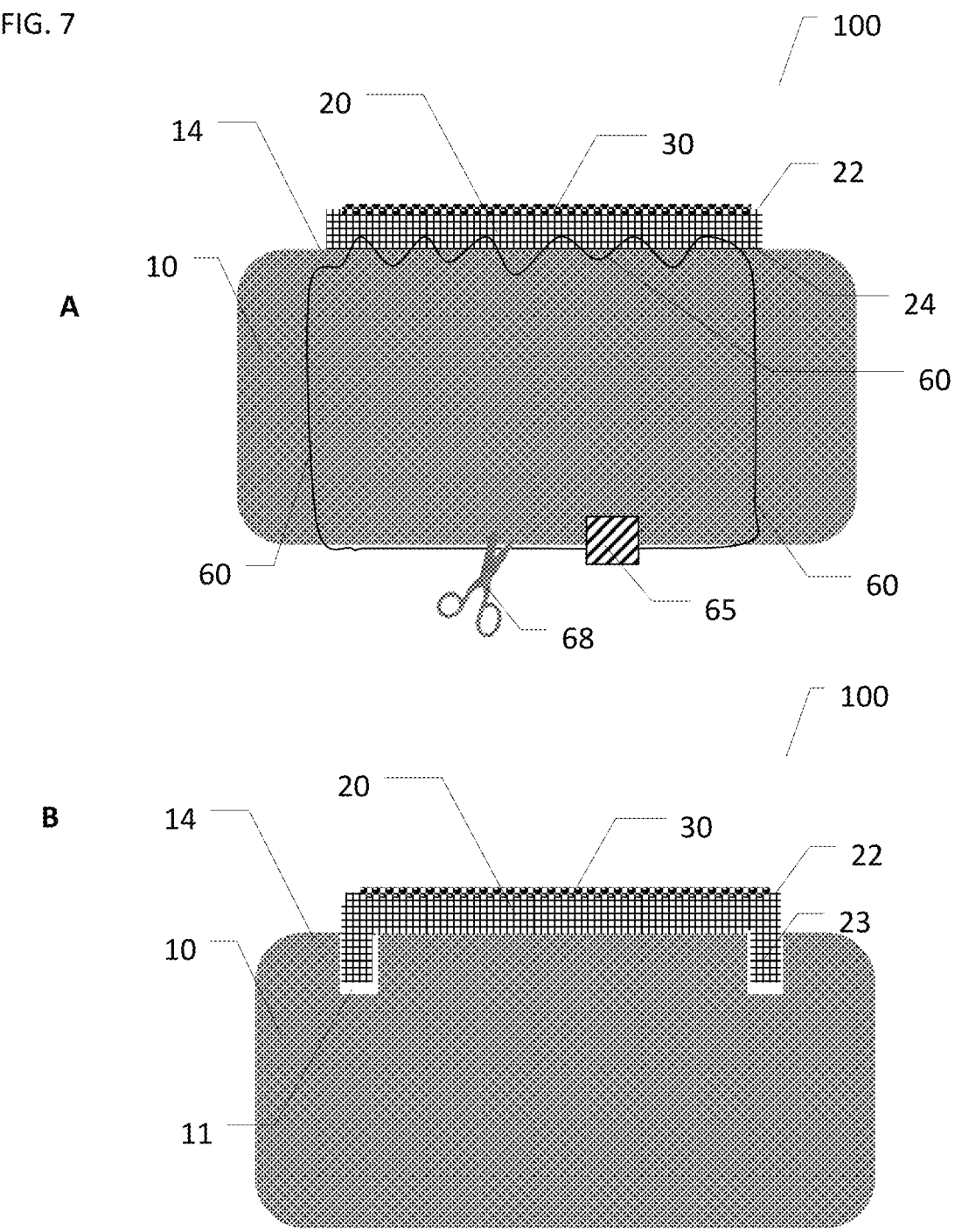
FIGS. 7 (A-B) show schematic cross-sectional views of embodiments of sealant and/or hemostat delivery device.

Referring now to FIG. 7A, a schematic cross-sectional view is shown of an embodiment of the present invention showing hemostat delivery device 100 comprising resorbable hemostatic pads 25 releasably attached to scaffold 10 by a mechanical mechanism comprising a flexible fiber or yarn or string 60 that is releasably stitched or sewn though resorbable support 20 and anchored in scaffold 10 and is exposed on scaffold 10 side, preferably on a side opposite attachment zone 14. Optionally string 60 is anchored by anchor 65 on a side opposite attachment zone 14. Once resorbable hemostatic pad 25 is positioned onto wound W, and after agent 30 is activated and bonds hemostatic pad 25 onto wound W, string 60 is cut using cutting means 68 such as scissors or scalpel.

After cutting, resorbable hemostatic pad 25 is released from scaffold 10, and withdrawal of scaffold 10 leaves resorbable hemostatic pad 25 on wound W. As scaffold 10 is withdrawn, it retrieves string 60 which is thereby removed from wound W. Scaffold 10 and string 60 are then discarded.

Referring now to FIG. 7B, a schematic cross-sectional view is shown of an embodiment of the present invention showing hemostat delivery device 100 comprising resorbable hemostatic pad 25 releasably attached to scaffold 10 by a mechanical mechanism comprising flaps 23 on the periphery or edges of resorbable support 20 inserted onto slits 11 formed in attachment zone 14 of scaffold 10. Slits 11 releasably engage flaps 23 resulting in releasable support of hemostatic pad 25 on scaffold 10. Preferably, as shown in FIG. 7B, there is no agent 30 on flaps 23. Once resorbable hemostatic pad 25 is positioned onto wound W, and agent 30 is activated and bonds hemostatic pad 25 onto wound, scaffold 10 is withdrawn with flaps 23 releasing from slits 11, leaving resorbable hemostatic pad 25 on wound W. Scaffold 10 is then discarded.

In an alternative embodiment (not shown) resorbable hemostatic pads 25 are releasably attached to scaffold 10 by a mechanical mechanism comprising a plurality of micro-hooks exposed on the surface of scaffold 10 in attachment zone 14 and releasably engaging back side 24 of resorbable support 20.

In another embodiment (not shown), resorbable hemostatic pads 25 are releasably attached to scaffold 10 by needle-punching resorbable support 20 into the surface of scaffold 10 in attachment zone 14.

Figure 8:
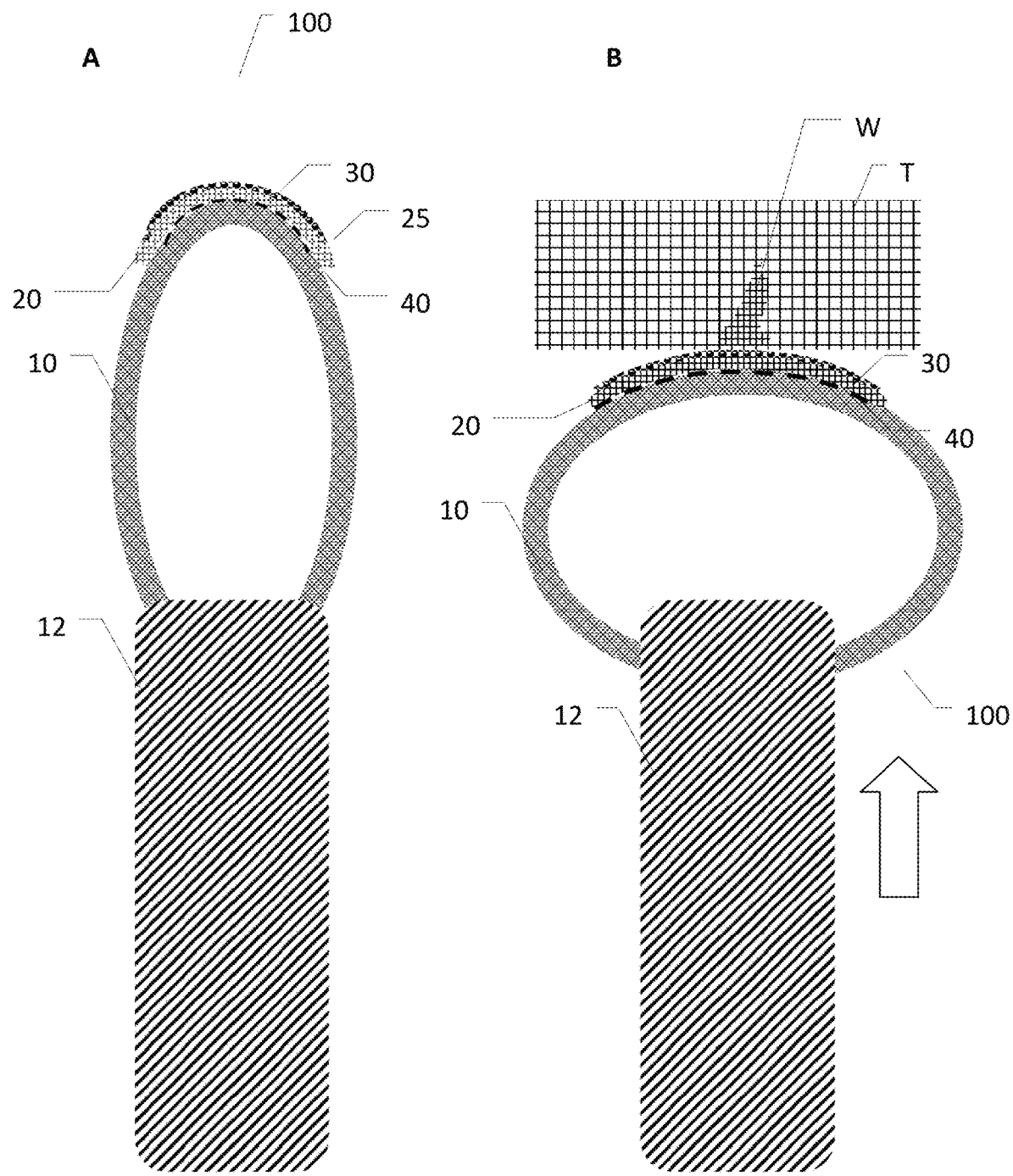
FIGS. 8 (A-B) show schematic cross-sectional views of sealant and/or hemostat delivery devices in operation.

Referring now to FIG. 8, a schematic cross-sectional view is shown of an embodiment of the present invention showing hemostat delivery device 100 comprising resorbable hemostatic pad 25 releasably attached to scaffold 10 which is a mechanical spreader. Scaffold 10 is not a balloon, but a circular or semi-circular bendable and flexible member, which has an elongated shape aligned with handle 12 as shown in FIG. 8A. As shown in FIG. 8B, upon pushing delivery device 100 with hemostatic pad 25 positioned against wound W in tissue T in the direction of the arrow, scaffold 10 deforms, spreading laterally and increasing its width over wound W, thus spreading resorbable hemostatic pad 25 simultaneously applying pad 25 to tissue.

The mechanism of attachment 40 of pad 25 to scaffold 10 can be any of the described above, including adhesive, string, mechanical entanglement. Once resorbable hemostatic pad 25 is positioned onto wound W, and agent 30 is activated and bonds hemostatic pad 25 onto wound, scaffold 10 releases pad 25 and is withdrawn leaving resorbable hemostatic pad 25 on wound W. Scaffold 10 is then discarded.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A sealant and/or hemostat delivery device, comprising:
   a resorbable hemostatic pad comprising a resorbable support having a wound facing side and an opposite back side, with a hemostatic and/or wound sealing agent disposed and exposed on the wound facing side;
   said resorbable support comprising a woven or non-woven fabric or cloth comprising oxidized cellulose, oxidized regenerated cellulose, synthetic absorbable polyesters, poly-dioxanone, poly-caprolactone, lactide, glycolide, poly(lactic-co-glycolic acid), or combinations thereof;
   a non-resorbable scaffold having an attachment zone on said scaffold; wherein said back side of the hemostatic pad is releasably attached to the attachment zone by a rapidly water soluble adhesive material,
   wherein, upon exposure to blood and/or exudates from a wound, the scaffold is configured to release the hemostatic pad due to dissolution of said adhesive material,
   wherein said adhesive material has a melting point between about 50° C. and about 75° C.,
   wherein said scaffold is not a balloon and is not inflatable or deflatable, wherein said scaffold is absorbent, surgically compatible material that is configured to expand upon exposure to bodily fluids, and wherein said scaffold comprises a barrier layer covering said attachment zone, said barrier layer comprising a coating or a layer of liquid-impervious material.

2. The delivery device of claim 1, wherein said scaffold further comprises a handle configured for deep wound applications.

3. The delivery device of claim 1, wherein said scaffold comprises a mass of non-absorbable foam.

4. The delivery device of claim 1, wherein said scaffold comprises a surgical gauze.

5. The delivery device of claim 1, wherein the hemostatic and/or wound sealing agent is selected from the group consisting of fibrinogen, thrombin, chitosan, gelatin, oxidized cellulose, oxidized regenerated cellulose, and combinations thereof.

6. The delivery device of claim 1, wherein the hemostatic and/or wound sealing agent comprises fibrinogen and thrombin.

7. The delivery device of claim 1, wherein said resorbable support is a single layer woven or non-woven fabric or cloth.

8. The delivery device of claim 1, wherein said resorbable support is a multi-layer woven or non-woven fabric or cloth.

9. The delivery device of claim 1, wherein said resorbable support is porous.

* * * * *